United States Patent [19]

Hughes et al.

[11] Patent Number: 4,985,441
[45] Date of Patent: Jan. 15, 1991

[54] ANTI-TUMOR AGENTS

[75] Inventors: Leslie R. Hughes, Macclesfield; John Oldfield, Wilmslow; Stephen J. Pegg, Macclesfield, all of United Kingdom

[73] Assignees: Imperial Chemical Industries plc; National Research Development Corp., both of London, England

[21] Appl. No.: 504,740

[22] Filed: Apr. 3, 1990

Related U.S. Application Data

[63] Continuation of Ser. No. 344,095, Apr. 27, 1989, abandoned.

[30] Foreign Application Priority Data

Apr. 27, 1988 [GB] United Kingdom ............... 8809978

[51] Int. Cl.$^5$ ................ A61K 31/505; C07D 239/90
[52] U.S. Cl. ................... 514/260; 514/259; 544/284; 544/285; 544/207
[58] Field of Search ............ 544/284, 285, 287; 514/260, 259

[56] References Cited

U.S. PATENT DOCUMENTS 4,447,608 5/1984 Jones et al. .................... 544/287

FOREIGN PATENT DOCUMENTS

| A20204529 | 12/1986 | European Pat. Off. . |
| A20239362 | 9/1987 | European Pat. Off. . |
| A20284338 | 9/1988 | European Pat. Off. . |
| A20316657 | 5/1989 | European Pat. Off. . |
| A2188319 | 9/1987 | United Kingdom . |

OTHER PUBLICATIONS

Hughes, "Chemical Abstracts", vol. 108, 1988, Col. 108:205094d.

Jones et al., "Chemical Abstracts," vol. 110, 1989, Col. 110:173724g.
Patil et al., "Chemical Abstracts", vol. 110, 1989, Col. 110:232041g.

Primary Examiner—Glennon H. Hollrah
Assistant Examiner—James H. Turnipseed
Attorney, Agent, or Firm—Cushman, Darby & Cushman

[57] ABSTRACT

The invention relates to quinazoline derivatives which possess anti-tumor activity; to processes for their manufacture; and to pharmaceutical compositions containing them.

The invention provides a quinazoline of the formula:

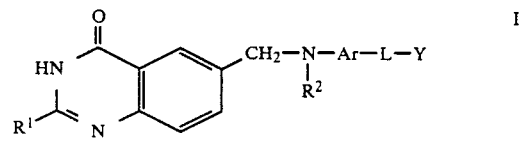

wherein $R^1$ is hydrogen or amino, or alkyl or alkoxy each of up to 6 carbon atoms; or $R^1$ is substituted alkyl or alkoxy each of up to 3 carbon atoms;
$R^2$ is hydrogen, alkyl, alkenyl, alkynyl, hydroxyalkyl or halogenoalkyl each of up to 6 carbon atoms;
Ar is phenylene or heterocyclene;
L is a group of the formula —CO.NH— or —CO.N-$R^3$—, wherein $R^3$ is alkyl of up to 6 carbon atoms; and
Y is hydrogen or alkyl, cycloalkyl, alkenyl or alkynyl each of up to 6 carbon atoms; or
Y is a group of the formula —A—$Y^1$ in which A is alkylene of up to 6 carbon atoms and $Y^1$ includes hydroxy, amino and cyano, and alkoxy, alkylamino and alkylthio each of up to 6 carbon atoms.

9 Claims, No Drawings

ANTI-TUMOR AGENTS

This is a continuation of application Ser. No. 07/344,095, filed Apr. 27, 1988, which is abandoned.

This invention relates to novel anti-tumour agents and more particularly it relates to quinazoline derivatives which possess anti-tumour activity. The invention includes novel quinazoline derivatives and processes for their manufacture; novel pharmaceutical compositions containing said quinazoline derivatives and the use of said quinazoline derivatives in the manufacture of novel medicaments for use in the production of an anti-tumour effect in a warm-blooded animal such as man.

One group of anti-tumour agents comprises the anti-metabolites which are antagonists of folic acid, such as aminopterin and methotrexate. A newer compound of this type which showed considerable promise in clinical trials is known as CB3717 and is described and claimed in United Kingdom Patent Specification No. 2065653B. Despite its promising activity against human breast, ovarian and liver cancer, however, CB3717 shows symptoms of toxicity in humans, particularly in relation to the liver and kidney [Calvert, Alison, Harland, Robinson, Jackman, Jones, Newell, Siddik, Whiltshaw, McElwain, Smith and Harrap, *J. Clin. Oncol.*, 1986, 4, 1245; Cantwell, Earnshaw and Harris, *Cancer Treatment Reports*, 1986, 70, 1335; Bassendine, Curtin, Loose, Harris and James, *J. Hepatol.*, 1987, 4, 39; Vest, Bork and Hasen, *Eur. J. Cancer Clin. Oncol.*, 1988, 24, 201; Cantwell, Macaulay, Harris, Kaye, Smith, Milsted and Calvert, *Eur. J. Cancer Clin. Oncol.*, 1988, 24, 733; Sessa, Zucchetti, Ginier, Willems, D'Incalci and Cavalli, *Eur. J. Cancer Clin. Oncol.*, 1988, 24, 769].

Compounds of the CB3717 type are believed to act as anti-tumour agents by inhibiting the enzyme thymidylate synthetase. The anti-tumour activity of CB3717 may be assessed in vitro by determining its inhibitory effect on that enzyme, and in cell cultures by its inhibitory effect on cancer cell lines such as the mouse leukaemia cell lines L1210 and L5178Y TK-/- and the breast cancer cell line MCF-7.

Other compounds of the CB3717 type may therefore have their anti-tumour activity assessed and compared with that of CB3717, by their activity against, for example, the same enzyme and the same cancer cell lines.

We have now found that the quinazoline derivatives of the present invention possess CB3717 type activity.

According to the invention there is provided a quinazoline of the formula I (set out hereinafter)
  wherein $R^1$ is hydrogen or amino, or alkyl or alkoxy each of up to 6 carbon atoms;
  or $R^1$ is alkyl of up to 3 carbon atoms which bears a hydroxy substituent, or which bears one, two or three fluoro substituents;
  or $R^1$ is hydroxyalkoxy of up to 3 carbon atoms or alkoxyalkoxy of up to 6 carbon atoms;
  wherein $R^2$ is hydrogen, alkyl, alkenyl, alkynyl, hydroxyalkyl or halogenoalkyl each of up to 6 carbon atoms;
  wherein Ar is phenylene or heterocyclene which may be unsubstituted or may bear one or two substituents selected from halogeno, hydroxy and amino;
  wherein L is a group of the formula —CO.NH— or —CO.NR$^3$—,
  wherein $R^3$ is alkyl of up to 6 carbon atoms; and
  wherein Y is hydrogen or alkyl, cycloalkyl, alkenyl or alkynyl each of up to 6 carbon atoms; or
  Y is a group of the formula —A—Y$^1$ in which A is alkylene of up to 6 carbon atoms, and Y$^1$ is hydroxy, amino, nitro, cyano, mercapto or halogeno, or alkoxy, alkylamino, dialkylamino, halogenoalkyl, alkylthio, alkylsulphinyl, alkylsulphonyl or cycloalkyl each of up to 6 carbon atoms;
  and provided that, in the group of the formula —L—Y, no constituent methylene or methine group is attached to more than one heteroatom;
  or a pharmaceutically-acceptable salt thereof.

The chemical formulae referred to herein by Roman numerals are set out for convenience on a separate sheet hereinafter. In this specification the term "alkyl" includes both straight and branched alkyl groups but references to individual alkyl groups such as "propyl" are specific for the straight chain version only. An analogous convention applies to other generic terms.

It will be observed that a quinazoline of the invention may possess one or more asymmetric carbon atoms and it can therefore exist in racemic and optically active forms. It is to be understood that this invention encompasses a racemic form of the quinazoline and any optically-active form thereof which possesses anti-tumour activity, it being a matter of common general knowledge how a racemic compound may be separated into its optically-active forms.

Suitable values for the generic radicals referred to above include those set out below.

A suitable value for $R^1$, $R^2$, $R^3$ or Y when it is alkyl of up to 6 carbon atoms is, for example, methyl, ethyl, propyl, isopropyl, butyl, isobutyl, sec-butyl, tert-butyl, pentyl, isopentyl, tert-pentyl, hexyl or isohexyl.

A suitable value for Y or $Y^1$ when it is cycloalkyl is, for example, cyclopropyl, cyclopentyl or cyclohexyl.

A suitable value for Y when it is alkenyl is, for example, prop-2-enyl, but-2-enyl, but-3-enyl, 2-methylprop-2-enyl, hex-2-enyl, hex-5-enyl or 2,3-dimethylbut-2-enyl.

A suitable value for Y when it is alkynyl is, for example, prop-2-ynyl, but-2-ynyl, but-3-ynyl, pent-2-ynyl, 3-methylpent-4-ynyl, hex-2-ynyl or hex-5-ynyl.

A suitable value for $R^1$ or $Y^1$ when it is alkoxy of up to 6 carbon atoms is, for example, methoxy, ethoxy, propoxy, isopropoxy, butoxy, isobutoxy, pentyloxy or hexyloxy.

A suitable value for $Y^1$ when it is alkylthio of up to 6 carbon atoms is, for example, methylthio, ethylthio, propylthio, isopropylthio, butylthio, isobutylthio, tert-butylthio, sec-butylthio, pentylthio or hexylthio.

A suitable value for $Y^1$ when it is halogeno or for a halogeno substituent which may be present as a substituent on Ar is, for example, fluoro, chloro, bromo or iodo.

A suitable value for $R^1$ when it is substituted alkyl is, for example, fluoromethyl, difluoromethyl, trifluoromethyl, 2-fluoroethyl, 3-fluoropropyl, hydroxymethyl, 2-hydroxyethyl or 3-hydroxypropyl.

A suitable value for $R^1$ when it is substituted alkoxy is, for example, 2-hydroxyethoxy, 2-methoxyethoxy, 3-methoxypropoxy or 2-ethoxyethoxy.

A suitable value for $R^2$ when it is alkenyl is, for example, prop-2-enyl, 2-methylprop-2-enyl, but-2-enyl or but-3-enyl; when it is alkynyl is, for example, prop-2-ynyl or but-3-ynyl; and when it is hydroxyalkyl or halogenoalkyl is, for example, 2-hydroxyethyl, 3-hydroxypropyl, 2-fluoroethyl, 2-chloroethyl, 2-bromoethyl, 3-fluoropropyl or 3-chloropropyl.

A suitable value for Ar when it is phenylene is, for example, 1,3-phenylene or 1,4-phenylene.

A suitable value for Ar when it is heterocyclene is, for example, a 5-membered or 6-membered aromatic (that is, fully unsaturated) heterocyclene diradical which contains up to 3 heteroatoms selected from the group consisting of oxygen, nitrogen and sulphur, for example, thienylene, pyridylene or thiazolylene.

A suitable value for A when it is alkylene is, for example, methylene, ethylene, ethylidene, trimethylene, propylidene, propylene, 2-trifluoromethylethylene, 1-ethylethylene, 1-propylethylene, 1-isopropylethylene, tetramethylene, pentamethylene or hexamethylene.

A suitable value for $Y^1$ when it is alkylamino, dialkylamino, halogenoalkyl, alkylsulphinyl or alkylsulphonyl is, for example, methylamino, ethylamino, propylamino, isopropylamino, butylamino, pentylamino, hexylamino, dimethylamino, N-ethyl-N-methylamino, diethylamino, N-methyl N-propylamino, N-methyl-N-isopropylamino, N-ethyl-N-isopropylamino, di-isopropylamino, fluoromethyl, difluoromethyl, trifluoromethyl, 2-fluoroethyl, 3-fluoropropyl, pentafluoroethyl, heptafluoropropyl, chloromethyl, dichloromethyl, methylsulphinyl, ethylsulphinyl, propylsulphinyl, isopropylsulphinyl, butylsulphinyl, isobutylsulphinyl, sec-butylsulphinyl, tert-butylsulphinyl, methylsulphonyl, ethylsulphonyl, propylsulphonyl, isopropylsulphonyl, butylsulphonyl, isobutylsuphonyl, sec-butylsulphonyl or tert-butylsulphonyl.

A suitable pharmaceutically-acceptable salt of a quinazoline of the invention which is sufficiently basic is an acid-addition salt with, for example, an inorganic or organic acid, for example hydrochloric, hydrobromic, sulphuric, phosphoric, trifluoroacetic, citric or maleic acid.

A particular quinazoline of the invention has the formula I
wherein $R^1$ is alkyl or alkoxy each of up to 6 carbon atoms;
or $R^1$ is alkyl of up to 3 carbon atoms which bears a hydroxy substituent, or which bears one, two or three fluoro substituents;
or $R^1$ is hydroxyalkoxy of up to 3 carbon atoms or alkoxyalkoxy of up to 6 carbon atoms;
wherein $R^2$ is hydrogen, alkyl, alkenyl, alkynyl, hydroxyalkyl or halogenoalkyl each of up to 6 carbon atoms;
wherein Ar is phenylene or heterocyclene which may be unsubstituted or may bear one or two substituents selected from halogeno, hydroxy and amino;
wherein L is a group of the formula —CO.NH— or —CO.NR$_3$—,
wherein $R^3$ is alkyl of up to 6 carbon atoms; and
wherein Y is hydrogen or alkyl, cycloalkyl, alkenyl or alkynyl each of up to 6 carbon atoms; or
Y is a group of the formula —A—$Y^1$ in which A is alkylene of up to 6 carbon atoms, and $Y^1$ is hydroxy, amino, nitro or cyano, or alkoxy, alkylamino, dialkylamino, halogenoalkyl, alkylthio, alkylsulphinyl or alkylsulphonyl each of up to 6 carbon atoms;
and provided that, in the group of the formula —L—Y, no constituent methylene or methine group is attached to more than one heteroatom and no constituent methylidene or methylidyne group is attached to a heteroatom;
or a pharmaceutically-acceptable salt thereof.

A further particular quinazoline of the invention has the formula I wherein $R^1$ is hydrogen or amino, or alkyl (especially methyl, ethyl and isopropyl) or alkoxy (especially methoxy and ethoxy) each of up to 6 carbon atoms; or $R^1$ is alkyl of up to 3 carbon atoms which bears a hydroxy substituent or which bears one, two or three fluoro substituents (especially fluoromethyl, difluoromethyl, trifluoromethyl, 2-fluoroethyl, hydroxymethyl and 2-hydroxyethyl); or $R^1$ is hydroxyalkoxy of up to 3 carbon atoms or alkoxyalkoxy of up to 6 carbon atoms (especially 2-hydroxyethoxy, 2-methoxyethoxy and ethoxyethoxy);
wherein $R^2$ is hydrogen, alkyl (especially methyl, ethyl and propyl), alkenyl (especially prop-2-enyl), alkynyl (especially prop-2-ynyl), hydroxyalkyl (especially 2-hydroxyethyl and 3-hydroxypropyl) or halogenoalkyl (especially 2-fluoroethyl, 2-chloroethyl, 2-bromoethyl and 3-fluoropropyl) each of up to 6 carbon atoms;
wherein Ar is phenylene (especially 1,4-phenylene) or heterocyclene (especially thienylene, pyridylene and thiazolylene) which is unsubstituted or which bears one or two substituents selected from halogeno (especially fluoro, chloro and bromo), hydroxy and amino;
wherein L is a group of the formula —CO.NH— or —CO.NR$_3$—,
wherein $R^3$ is alkyl (especially methyl and ethyl) of up to 6 carbon atoms; and
wherein Y is hydrogen or alkyl (especially methyl, ethyl, propyl, isopropyl, butyl, isobutyl and tert butyl), cycloalkyl (especially and cyclohexyl), alkenyl (especially prop-2-enyl and but-2-enyl), or alkynyl (especially prop-2-ynyl and but-2-ynyl) each of up to 6 carbon atoms; or
Y is a group of the formula —A—$Y^1$ in which A is alkylene (especially methylene, ethylene, ethylidene, trimethylene, propylidene, propylene, 2-trifluoromethylethylene, 1-isopropylethylene, tetramethylene, pentamethylene and hexamethylene) of up to 6 carbon atoms, and $Y^1$ is hydroxy, amino, nitro, cyano, mercapto or halogeno (especially fluoro, chloro and bromo), or alkoxy (especially methoxy and ethoxy), alkylamino (especially methylamino, ethylamino, isopropylamino and butylamino), dialkylamino (especially dimethylamino, diethylamino and di-isopropylamino), halogenoalkyl (especially fluoromethyl, difluoromethyl, trifluoromethyl and pentafluoroethyl), alkylthio (especially methylthio, ethylthio, propylthio, isopropylthio, butylthio, isobutylthio and tert-butylthio), alkylsulphinyl (especially methylsulphinyl, ethylsulphinyl, isopropylsulphinyl, butylsulphinyl, isobutylsulphinyl and tert butylsulphinyl), alkylsulphonyl (especially methylsulphonyl, ethylsulphonyl and isopropylsulphonyl) or cycloalkyl (especially cyclopentyl and cyclohexyl) each of up to 6 carbon atoms; and provided that, in the group of the formula —L—Y, no constituent methylene or methine group is attached to more than one heteroatom;
or a pharmaceutically-acceptable salt thereof.

A preferred quinazoline of the invention has the formula I wherein $R^1$ is hydrogen, amino, methyl, ethyl, methoxy or fluoromethyl;
wherein $R^2$ is hydrogen, methyl, ethyl, propyl, prop-2-enyl, prop-2-ynyl, 2-hydroxyethyl, 3-hyroxypropyl, 2-fluoroethyl or 2-bromoethyl;
wherein Ar is 1,4-phenylene, thien-2,5-diyl, pyrid-2,5-diyl or thiazol-2,5-diyl which is unsubstituted or which bears one or two substituents selected from fluoro, chloro, hydroxy and amino;

wherein L is a group of the formula —CO.NH— or —CO.NR$_3$—, wherein R$^3$ is methyl or ethyl; and wherein Y is hydrogen, methyl, ethyl, propyl, isopropyl, isobutyl or tert-butyl; or Y is a group of the formula —A—Y$^1$ in which A is methylene, ethylene, ethylidene, trimethylene, propylene, 2-trifluoromethylethylene, 1-isopropylethylene, tetramethylene, pentamethylene or hexamethylene and Y$^1$ is hydroxy, amino, nitro, cyano, mercapto, chloro, methoxy, methylamino, ethylamino, butylamino, dimethylamino, diethylamino, methylthio, ethylthio, propylthio, isopropylthio, tert-butylthio, methylsulphinyl, ethylsulphinyl, isopropylsulphinyl, tert-butylsulphinyl or methylsulphonyl; or a pharmaceutically-acceptable salt thereof.

A further preferred quinazoline of the invention has the formula I wherein R$^1$ is methyl;
R$^2$ is methyl, ethyl or prop-2-ynyl;
Ar is 1,4-phenylene;
L is a group of the formula —CO.NH—; and
Y is propyl, isopropyl or isobutyl; or Y is a group of the formula —A—Y$^1$ in which A is methylene, ethylene, trimethylene, 2-methylethylene, 2-trifluoromethylethylene, 1-isopropylethylene, tetramethylene or pentamethylene and Y$^1$ is hydroxy, amino, cyano, chloro, methoxy, butylamino, dimethylamino, diethylamino, methylthio, ethylthio, methylsulphinyl or methylsulphonyl;
or a pharmaceutically-acceptable salt thereof.

An especially preferred quinazoline of the invention has the formula I wherein R$^1$ is methyl;
wherein R$^2$ is hydrogen, methyl, ethyl, prop-2-ynyl or 2-fluoroethyl;
wherein Ar is 1,4-phenylene or thien-2,5-diyl, or is pyrid-2,5-diyl or thiazol-2,5-diyl each with the group —L—Y in the 2-position, or is 2-fluoro-1,4-phenylene with the group —L—Y in the 1-position;
wherein L is a group of the formula —CO.NH—; and
wherein Y is hydrogen, methyl, ethyl, propyl, isopropyl or isobutyl;
or a pharmaceutically-acceptable salt thereof.

A further especially preferred quinazoline of the invention has the formula I wherein R$^1$ is methyl;
R$^2$ is ethyl or prop-2-ynyl;
Ar is 1,4-phenylene;
L is a group of the formula —CO.NH—;
and Y is propyl, isobutyl, 2-hydroxy-2-trifluoromethylethyl, 2-hydroxy-1-isopropylethyl, 2-hydroxyethyl, 3-hydroxypropyl, 4-hydroxybutyl, 6-hydroxyhexyl, 2-aminoethyl, cyanomethyl, 2-cyanoethyl, 5-cyanopentyl, 3-chloropropyl, 2-methoxyethyl, 2-butylaminoethyl, 2-dimethylaminoethyl, 3-dimethylaminopropyl, 3-diethylaminopropyl, 2-methylthioethyl, 2-ethylthioethyl, 2-methylsulphinylethyl or 2-methylsulphonylethyl;
or a pharmaceutically-acceptable salt thereof.

Specific preferred quinazolines of the invention include:
p-[N-(3,4-dihydro-2-methyl-4-oxoquinazolin-6-ylmethyl)-N-(prop-2-ynyl)amino]-N-propylbenzamide,
N-cyanomethyl[-N-(3,4-dihydro-2-methyl-4-oxoquinazolin-6-ylmethyl)-N-(prop-2-ynyl)amino]-benzamide,
p-[N-(3,4-dihydro-2-methyl-4-oxoquinazolin-6-ylmethyl)-N-(prop-2-ynylamino]-N-(2-hydroxy-2-trifluoromethylethyl)benzamide,
p-[N-(3,4-dihydro-2-methyl-4-oxoquinazolin-6-ylmethyl)-N-(prop-2-ynyl)amino]-N-(2-ethylthioethyl)benzamide,
p-[N-(3,4-dihydro-2-methyl-4-oxoquinazolin-6-ylymethyl)-N-(prop-2-ynyl)amino-N-(2-methoxyethyl)benzamide,
N-(2-N-butylaminoethyl)-p-[N-(3,4-dihydro-2-methyl-4-oxoquinazolin-6-ylmethyl)-N-(prop-2ynyl)amino]-benzamide,
p-[N-(3,4-dihydro-2-methyl-4-oxoquinazolin-6-ylmethyl)-N-(prop-2-ynyl)amino]-N-(2N,N-dimethylaminoethyl)benzamide,
p-[N-(3,4-dihydro-2-methyl-4-oxoquinazolin-6-ylmethyl)-N-(prop-2-ynyl)amino]-N-(3-N,N-dimethylaminopropyl)benzamide,
N-(3-N,N-diethylaminopropyl)-p-[N-(3,4-dihydro-2-methyl-4-oxoquinazolin-6-ylmethyl)-N-(prop-2-ynyl)amino]benzamide,
p-[N-(3,4-dihydro-2-methyl-4-oxoquinazolin-6-ylmethyl)-N-(prop-2-ynyl)amino]-N-(2-methylthioethyl)-benzamide,
p-[N-(3,4-dihydro-2-methyl-4-oxoquinazolin-6-ylmethyl)-N-(prop-2-ynyl)amino]-N-(2-hydroxyethyl)-benzamide,
p-[N-(3,4-dihydro-2-methyl-4-oxoquinazolin-6-ylmethyl-N-(prop-2-ynyl)amino]-N-(3-hydroxypropyl)benzamide,
p-[N-(3,4-dihydro-2-methyl-4-oxoquinazolin-6-ylmethyl)-N-(prop-2-ynyl)amino]-N-(4-hydroxybutyl)-benzamide,
p-[N-(3,4-dihydro-2-methyl-4-oxoquinazolin-6-ylmethyl-N-(prop-2-ynyl)amino]-N-(6-hydroxyhexyl)benzamide,
N-(3-chloropropyl)-p-[N-(3,4-dihydro-2-methyl-4-oxoquinazolin-6-ylmethyl)-N-(prop-2-ynyl)amino]-benzamide,
N-(2-aminoethyl)-p-[N-(3,4-dihydro-2methyl-4-oxoquinazolin-6-ylmethyl)-N-prop-2-ynyl)amino]-benzamide,
N-(5-cyanopentyl)-p-[N-(3,4-dihydro-2-methyl-4-oxoquinazolin-6-ylmethyl)-N-(prop-2-ynyl)amino]-benzamide and
N-(2-cyanoethyl)-p-N-(3,4-dihydro-2-methyl-4-oxoquinazolin-6-ylmethyl)-N-(prop-2-ynyl)amino]-benzamide.

A quinazoline of the invention, or a pharmaceutically-acceptable salt thereof, may be prepared by any process known to be applicable to the preparation of chemically related compounds.

A preferred process for the manufacture of a quinazoline of the invention comprises the reaction of a compound of the formula II wherein R$^1$ has the meaning stated above, provided that when R$^1$ is amino, hydroxyalkyl or hydroxyalkoxy any amino or hydroxy group is protected by a conventional protecting group, R$^4$ is hydrogen or a protecting group and Z is a displaceable group, with a compound of the formula:

HNR$^2$—Ar—L—Y wherein R$^2$, Ar, L and Y have the meanings stated above, provided that when there is a mercapto, amino, alkylamino or hydroxy group in R$^2$, Ar or Y, any mercapto, amino and alkylamino group is protected by a conventional protecting group and any hydroxy group may be protected by a conventional protecting group or alternatively any hydroxy group need not be protected;

whereafter any undesired protecting group in $R^1$, $R^2$, $R^4$, Ar and Y is removed.

A suitable protecting group for a hydroxy or mercapto group may be, for example, an esterifying group, for example an acetyl or benzoyl group, which may be removed by hydrolysis with a base, for example sodium hydroxide, or provided that $R^2$, L and Y do not contain an alkenyl or alkynyl group, the protecting group may be, for example, an α-arylalkyl group, for example a benzyl group, which may be removed by hydrogenation over a catalyst, for example palladium-on-charcoal.

A suitable protecting group for an amino or alkylamino group may be, for example, an alkoxycarbonyl group, for example a tert-butyloxycarbonyl group which may be removed by treatment with an organic acid, for example trifluoroacetic acid; or it may be, for example, a benzyloxycarbonyl group which may be removed by treatment with a Lewis acid, for example boron tris(trifluoroacetate).

A suitable alternative protecting group for a primary amino group is, for example, a phthaloyl group which may be removed by treatment with an alkylamine, for example dimethylaminopropylamine, or with hydrazine.

A suitable value for $R^4$ when it is a protecting group is, for example, a pivaloyloxymethyl group which may be removed by hydrolysis with a base, for example sodium hydroxide.

Z may be, for example, a halogeno or sulphonyloxy group, for example a chloro, bromo, methanesulphonyloxy or toluene-p-sulphonyloxy group.

The compound of the formula:

$$HNR^2\text{—Ar—L—Y}$$

wherein L is a group of the formula —CONH— or —CONR$^3$— wherein $R^3$ has the meanings stated above, used as a starting material above, may be obtained by the reaction of an acid of the formula $O_2N\text{—Ar—CO}_2H$, or a reactive derivative thereof, wherein Ar has the meaning stated above with an amine of the formula $H_2N\text{—Y}$ or $R^3NH\text{—Y}$ wherein $R^3$ and Y have the meanings stated above and any mercapto, amino and alkylamino group in Ar and Y is protected by a conventional protecting group as stated above and any hydroxy group in Ar and Y may be protected by a conventional protecting group as stated above or alternatively any hydroxy group need not be protected. Thereafter the nitro group may be reduced by conventional means to an amino group which in turn may be alkylated with a compound of the formula $R^2\text{—Z}$ wherein $R^2$ and Z have the meanings stated above.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide, for example dicyclohexylcarbodiimide.

A further preferred process for the manufacture of a quinazoline of the invention wherein L is a group of the formula —CONH— CONR$^3$—, comprises the reaction of an acid of the formula III, or a reactive derivative thereof, with a compound of the formula $H_2N\text{—Y}$ or $R^3NH\text{—Y}$ wherein $R^1$, $R^2$, $R^3$, $R^4$, Ar and Y have the meanings stated above and any amino and alkylamino group in $R^1$, Ar and Y is protected by a conventional protecting group as stated above and any hydroxy or mercapto group in $R^1$, $R^2$, Ar and Y may be protected by a conventional protecting group as stated above or alternatively any hydroxy or mercapto group need not be protected; whereafter the protecting groups are removed by conventional means.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide, for example dicyclohexylcarbodiimide.

The carboxylic acid used as starting material may be obtained by the reaction of a compound of the formula II wherein $R^1$, $R^4$ and Z have the meanings stated above, with a compound of the formula:

$$HNR^2\text{—Ar—CO}_2R^5$$

wherein $R^2$ and Ar have the meanings stated above and $R^5$ is a protecting group which can be removed to provide a carboxylic acid.

$R^5$ for example, methyl or an ethyl group which may be removed by hydrolysis with a base, for example sodium hydroxide or $R^5$ may be, for example, a tert-butyl group which may be removed by cleavage with an organic acid, for example trifluoroacetic acid.

The protecting group for the carboxy group in $R^5$ may be, for example, an esterifying group which can be removed while the protecting group for any amino, alkylamino and hydroxy group in $R^1$, $R^2$ and Ar is retained.

A further preferred process for the manufacture of a quinazoline of the invention wherein $R^1$ is alkoxy, hydroxyalkoxy or alkoxyalkoxy comprises the reaction of a compound of the formula IV wherein $R^1$ has the last-mentioned meaning stated above, provided that when there is a hydroxy substituent in $R^1$ it is protected by a conventional protecting group as stated above, and Z is a displaceable group, with a compound of the formula:

$$HNR^2\text{—Ar—L—Y}$$

wherein $R^2$, Ar, L and Y have the meanings stated above, provided that when there is a mercapto, amino, alkylamino or hydroxy group in $R^2$, Ar or Y any mercapto, amino and alkylamino group is protected by a conventional protecting group as stated above and any hydroxy group may be protected by a conventional protecting group, as stated above or alternatively any hydroxy group need not be protected; whereafter the protecting groups are removed by conventional means, as stated above and the $R^1$ group situated at the 4-position of the quinazoline ring is cleaved by hydrolysis with a base, for example sodium hydroxide, to form a quinazoline of the invention.

A further preferred process for the manufacture of a quinazoline of the invention wherein Y is a group of the formula —A—$Y^1$ in which $Y^1$ is alkylsulphinyl or alkylsulphonyl comprises the oxidation of a compound of the formula I wherein Y is a group of the formula —A—$Y^1$ in which $Y^1$ is alkylthio with a suitable oxidising agent.

A suitable oxidising agent is, for example, any reagent know to oxidise a thio group to a sulphinyl or sulphonyl group, for example, hydrogen peroxide, a peracid such as 3-chloroperbenzoic acid or peroxyacetic acid, or chromium trioxide. When a compound carrying a sulphinyl group is required the required stoichiometric amount of any one of the above oxidising agents may be used in order to reduce the production of a compound carrying a sulphonyl group. Alternatively a milder oxidising agent may be used, for example sodium or potassium metaperiodate. It will be appreciated that when a compound of the formula I containing a sulphonyl group is required, it may be obtained by the oxidation of the corresponding sulphinyl compound as well as by the oxidation of the corresponding thio compound.

As stated above a quinazoline derivative of the present invention possesses anti-tumour activity. This activity may be assessed, for example, using one or more of the procedures set out below:

(a) An in vitro assay which determines the ability of a test compound to inhibit the enzyme thymidylate synthetase. Thymidylate synthetase may be obtained in partially purified form from L1210 mouse leukaemia cells and utilised using the procedures described by Jackman et al. (*Cancer Res.*, 1986, 46, 2810);

(b) An assay which determines the ability of a test compound to inhibit the growth of the leukaemia cell line L1210 in cell culture. The test is similar to that described in UK Patent Specification No. 2065653B;

(c) An assay which determines the ability of a test compound to inhibit the growth of the human breast cancer cell line MCF-7 in cell culture. The test is similar to that described by Lippman et al. (*Cancer Res.*, 1976, 36, 4595); and (d) An assay which determines the ability of a test compound to inhibit growth of the leukaemia cell line L5178Y TK-/- in vitro. The leukaemia cell line L5178Y TK-/- is deficient in the enzyme thymidine kinase which enzyme phosphorylates thymidine and thus operates to generate a pool of thymidylate when de novo synthesis of thymidylate is prevented by the presence of an effective amount of an inhibitor of thymidylate synthetase. The L5178Y TK-/-cell line is thereby more sensitive to the presence of an inhibitor of thymidylate synthetase. [L5178Y TK-/- may be obtained by mutation of the parent L5178Y cell line which is described by, for example, Fischer et al., *Methods in Medical Research*, 1964, 10, 247]. The assay utilises a double layer soft agar cloning technique similar to that described by Courtenay et al. (*British J. Cancer*, 1976, 34, 39). Each test compound is added at a range of concentrations to L5178Y TK-/- cells which have entered exponential growth phase in cell culture and the cells are incubated for between 4 and 24 hours, harvested, washed with fresh culture medium and plated into soft agar for clonogenic evaluation. After about 12 days colonies of cells are stained and counted.

A quinazoline of the present invention may itself be active or it may be a pro-drug which is converted in vivo to an active compound.

Although the pharmacological properties of the quinazolines of the invention vary with structural changes, in general quinazolines of the invention possess activity in one or more of the above tests (a) to (d):

Test (a) $IC_{50}$ in the range, for example, 0.1–10 $\mu$M;
Test (b) $IC_{50}$ in the range, for example, 0.1–100 $\mu$M;
Test (c) $IC_{50}$ in the range, for example, 0.1–100 $\mu$M;
Test (d) The dose required to reduce the fraction of surviving cells to 10% of those treated lies in the range, for example, 5–100 $\mu$M.

In general those quinazolines of the invention which are particularly preferred possess activity in one or more of the above tests (a) to (d):

Test (a) $IC_{50}$ in the range, for example, 0.1–5 $\mu$M;
Test (b) $IC_{50}$ in the range, for example, 0.1–10 $\mu$M;
Test (c) $IC_{50}$ in the range, for example, 0.1–5 $\mu$M;
Test (d) The dose required to reduce the fraction of surviving cells to 10% of those treated lies in the range, for example, 5–50 $\mu$M.

Thus, by way of example, the quinazoline, p-[N-(3,4-dihydro-2-methyl-4-oxoquinazolin-6-ylmethyl)-N-(prop-2-ynyl)amino]-N-propylbenzamide has an $IC_{50}$ of 1.8 $\mu$M against thymidylate synthetase [Test (a)] and an $IC_{50}$ of 7 $\mu$M against the L1210 cell line [Test (b)].

A quinazoline of the invention, or a pharmaceutically-acceptable salt thereof, may be administered to a warm-blooded animal, including a human, in the form of a pharmaceutical composition which comprises the quinazoline in association with a pharmaceutically-acceptable diluent or carrier.

The composition may be in a form suitable for oral administration, as a tablet or capsule, or, especially, for parenteral injection, as a sterile solution, suspension or emulsion, or for topical administration, as an ointment or cream, or for rectal administration as a suppository.

The composition may contain, in addition to the quinazoline of the invention, one or more other anti-tumour substances selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

The quinazoline will normally be administered to a warm-blooded animal at a dose within the range 50–5000 mg per square meter body area of the animal, i.e. approximately 1–100 mg/kg, and this is considered to provide a therapeutically-effective dose. A unit dose form such as a sterile solution, suspension or emulsion for partenteral injection, a tablet or capsule will usually contain, for example, 1–250 mg of active ingredient.

According to further feature of the present invention there is provided a method for producing an antitumour effect in a warm-blooded animal, such as man, in need of such treatment which comprises administering to said animal an effective amount of a quinazoline of the present invention, or a pharmaceutically-acceptable salt thereof. The invention also provides the use of a quinazoline of the present invention, or a pharmaceutically-acceptable salt thereof, in the manufacture of a novel medicament for use in the production of an antitumour effect in a warm blooded animal such as man.

A quinazoline of the present invention is expected to possess a wide range of anti tumour activities. CB3717 showed promising activity against human breast, ovarian and liver cancer and consequently it is expected that a quinazoline of the present invention will possess anti-tumour activity against these cancers. It is in addition expected that a quinazoline of the present invention will possess anti tumour activity against a range of leukaemias, lymphoid malignancies and solid tumours such as carcinomas and sarcomas. Such tumours require thymidine monophosphate as one of the essential nucleotides for the synthesis of cellular DNA. In the presence of an effective amount of a thymidylate synthetase inhibitor such as an effective amount of a quinazoline of the present invention it is expected that tumour growth will be inhibited.

The invention is illustrated but not limited by the following Examples.

The structures of all compounds of the invention were confirmed by proton magnetic resonance and mass spectroscopy and by elemental analysis. Proton magnetic resonance spectra were determined using a Jeol FX 90Q or a Bruker AM200 spectrometer operating at a field strength of 200 MHz. Chemical shifts are reported in parts per million downfield from tetramethylsilane as an internal standard ($\delta$ scale) and peak multiplicities are shown thus: s, singlet; d, doublet; d of d's, doublet of doublets; t, triplet; m, multiplet. Fast-atom bombardment (FAB) mass spectral data were obtained using a VG Analytical MS9 spectrometer and xenon gas and, where appropriate either positive ion data or negative ion data were collected.

Column chromatography was performed using Merck Art 9385 silica gel.

Intermediates were not generally fully characterised and purity was assessed by one or more of thin layer chromatographic, infra-red (IR) and proton magnetic resonance analysis.

EXAMPLE 1

Diphenylphosphoryl azide (0.4 ml) and triethylamine (0.53 ml) were added successively to a mixture of p-[N-(3,4-dihydro-2-methyl-4-oxoquinazolin-6-ylmethyl)-N-(prop-2-ynyl)amino]benzoic acid (as its trifluoroacetic acid salt; 0.5 g; UK Patent Specification No. 2188319A) and dimethylsulphoxide (20 ml) and the mixture was stirred at laboratory temperature for 5 hours. Isobutylamine (0.24 ml) was added and the mixture was stirred at laboratory temperature for 16 hours. The mixture was poured onto a mixture of ice and water (100 ml). The solid so obtained was filtered off, washed with water (3×20 ml) and dried; resuspended in ethyl acetate, triturated, filtered p-[N-(3,4-dihydro-2-methy-4-oxoquinazolin-6-ylmethyl)-N-(prop-2-ynyl)amino]-N-isobutylbenzamide (0.2 g), m.p. 250°–253° C.

NMR Spectrum: (CD$_3$SOCD$_3$) 0.88 (d, 6H, 2×CH$_3$, J=7 Hz), 1.82 (m, 1H, CH), 2.33 (s, 3H, 2 CH$_3$), 3.03 (t, 2H, NHCH, J=7 Hz), 3.19 (t, 1H, C≡CH, J=2 Hz), 4.32 (d, 2H, CH$_2$C≡CH, J=2 Hz), 4.78 (s, 2H, CH$_2$N), 6.82 (d, 2H, aromatic, J=9 Hz), 7.54 (d, 1H, 8H, J=8 Hz), 7.68 (d of d's, 1H, 7-H, J=8 and 2 Hz), 7.69 (d, 2H, aromatic, J=9 Hz), 7.97 (d, 1H, 5-H, J=2 Hz), 8.08 (t, 1H, CONH, J=6 Hz); Mass Spectrum: (positive ion FAB) m/e (P+1) 403; Elemental Analysis: Found C, 71.1; H,6.4; N, 13.8; C$_{24}$H$_{26}$N$_4$O$_2$ requires C, 71.6; H, 6.5; N, 13.9%.

EXAMPLE 2

The process described in Example 1 was repeated using the appropriate amine in place of isobutylamine. There were thus obtained the compounds described in the following table, the structures of which were confirmed by proton magnetic resonance and mass spectroscopy and by elemental analysis.

TABLE I

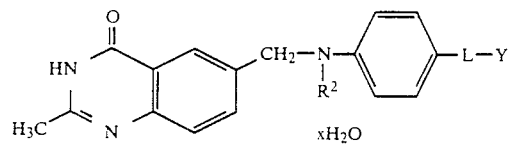

| Compd. No. (Note) | R$^2$ | L | Y | x | m.p. (°C.) |
|---|---|---|---|---|---|
| 1(1) | prop-2-ynyl | —CONH— | methyl | 2 | 138–145 (decomp.) |
| 2 | prop-2-ynyl | —CONH— | ethyl | 0.5 | 240–244 (decomp.) |
| 3 | prop-2-ynyl | —CONH— | n-propyl | 0.7 | 235–236 (decomp.) |
| 4(1) | prop-2-ynyl | —CONMe— | methyl | 1.3 | 192–198 (decomp.) |
| 5(2) | prop-2-ynyl | —CONH— | cyanomethyl | 0.5 | 269–274 |
| 6(3) | ethyl | —CONH— | 2-hydroxypropyl | 0.8 | 215–219 |
| 7(4) | ethyl | —CONH— | 3,3,3-trifluoro-2-hydroxypropyl | 1.5 | 199–204 |
| 8(5) | prop-2-ynyl | —CONH— | 1-hydroxymethyl-2-methylpropyl | 1 | 224–228 |
| 9(6) | prop-2-ynyl | —CONH— | hydrogen | 0.5 | 228–290 |

Notes
(1) A 33% solution of the appropriate amine in a 95:5 v/v mixture of ethanol and water was used.
(2) Aminoacetonitrile bisulphate was used as the appropriate amine and six equivalent of triethylamine were used rather than 3.5 equivalents as in Example 1.
(3) D,L-Isopropanolamine was used as the appropriate amine.
(4) 3,3,3-Trifluoro-2-hydroxypropylamine is described in J. Amer. Chem. Soc., 1954, 76, 83.
(5) L-Valinol was used as the appropriate amine.
(6) A concentrated aqueous solution of ammonium hydroxide (30% by weight of NH$_3$) was used.

EXAMPLE 3

2 Ethylthioethylamine (200 mg) was added to a mixture of p-[N-(3,4-dihydro-2-methyl-4-oxoquinazolin-6-ylmethyl)-N-(prop-2-ynyl)amino]benzoyl azide (250 mg) and N,N-dimethylformamide (4 ml) and the mixture was stirred in the absence of light at laboratory temperature for 4 hours. The solvent was evaporated under reduced pressure and the residual solid was triturated with water (70 ml) and the mixture was centrifuged. The supernatant solution was decanted, the remaining solid was recentrifuged with water (70 ml), and the supernatant solution was again decanted. The solid was transferred to a round-bottomed flask and was freeze-dried overnight and then dried in vacuo at 70° C. for 12 hours. There was thus obtained p-[N-(3,4-dihydro-2-methyl-4-oxoquinazolin-6-ylmethyl)-N-(prop-2-ynyl)amino]-N-(2-ethylthioethyl)benzamide (225 mg), m.p. 230°–235° C.

NMR Spectrum: ($CD_3SOCD_3$) 1.20 (t, 3H, $CH_3$, J=7.5 Hz), 2.33 (s, 3H, 2-$CH_3$), 2.53 (t, 2H, $CH_2S$, J=7.5 Hz), 2.64 (t, 2H, $CH_2S$, J=7.5 Hz), 3.18 (t, 1H, C≡CH, J=2 Hz), 3.38 (q, 2H, $NHCH_2$, J=7.5 Hz), 4.30 (d, 2H, $CH_2$C≡CH, J=2 Hz), 4.78 (s, 2H, $ArCH_2N$), 6.82 (d, 2H, aromatic, J=8 Hz), 7.53 (d, 1H, 8-H, J=8 Hz), 7.68 (d of d's, 1H, 7-H, J=8 and 2 Hz), 7.68 (d, 2H, aromatic, J=8 Hz), 7.96 (d, 1H, 5-H, J=2 Hz), 8.25 (t, 1H, CONH, J=7.5 Hz), 12.13 (broad s, 1H, 3-H, (NH)); Mass Spectrum: (positive ion FAB) m/e (P+1) 435; Elemental Analysis: Found C, 66.6; H, 6.2: N, 12.7: S, 7.2; $C_{24}H_{26}N_4O_2S$ requires C, 66.3; H, 6.0; N, 12.9; S, 7.4%.

The required benzoyl azide starting material was obtained as follows: Triethylamine (9.84 ml) and diphenylphosphoryl azide (6.1 ml) were added successively to a mixture of p-[N-(3,4-dihydro-2-methyl-4-oxoquinazolin-6-ylmethyl)-N-(prop-2-ynyl)amino]benzoic acid (as its trifluoroacetic acid salt, 8.0 g) and N,N-dimethylformamide (60 ml) and the mixture was stirred at laboratory temperature for 18 hours. The mixture was centrifuged and the supernatant was decanted. The remaining solid was washed with N,N-dimethylformamide (3×40 ml) and diethyl ether (40 ml) and dried. There was thus obtained p-[N-3,4-dihydro-2-methyl-4-oxoquinazolin-6-ylmethyl)-N-(prop-2-ynyl)amino]benzoyl azide (5.3 g), m.p. 215°–218° C. (decomp).

NMR Spectrum: ($CD_3SOCD_3$) 2.32 (s, 3H, $CH_3$), 3.23 (t, 1H, C≡CH, J=2 Hz), 4.39 (d, 2H, $CH_2$C≡CH, J=2 Hz), 4.85 (s, 2H, $CH_2N$), 6.88 (d, 2H, J=9 Hz, aromatic), 7.53 (d, 1H, 8-H, J=8 Hz), 7.67 (d of d's, 1H, 7-H, J=8 Hz and 2 Hz), 7.78 (d, 2H, aromatic, J=9 Hz), 7.94 (d, 1H, 5-H, J=2 Hz), 12.14 (broad s, 1H, 3H, (NH)); Mass spectrum: (positive ion FAB) m/e (P+1) 373; Elemental Analysis: Found C, 63.9; H, 4.7; N, 22.0; $C_{20}H_{16}N_6O_2$. 0.33$H_2O$ requires C, 63.5; H, 4.4; N 22.2%.

EXAMPLE 4

The process described in Example 3 was repeated using the appropriate amine in place of 2-ethylthioethylamine. There were thus obtained the compounds described in the following table, the structures of which were confirmed by proton magnetic resonance and mass spectrometry and by elemental analysis.

TABLE II

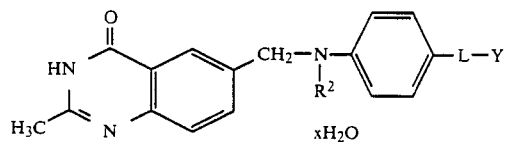

$xH_2O$

| Compd. No. (Note) | $R^2$ | L | Y | x | m.p. (°C.) |
|---|---|---|---|---|---|
| 1 | prop-2-ynyl | —CONH— | 2-methoxyethyl | 0.3 | 231–234 |
| 2(1) | prop-2-ynyl | —CONH— | 2-(N-butylamino)-ethyl | | 115.5–118 |
| 3(2) | prop-2-ynyl | —CONH— | 2-(N,N-dimethylamino)ethyl | | 77–82 |
| 4(3) | prop-2-ynyl | —CONH— | 3-(N,N-dimethylamino)propyl | 0.67 | 187–189 |
| 5 | prop-2-ynyl | —CONH— | 3-(N,N-diethylamino)propyl | 0.5 | 160–173 |
| 6 | prop-2-ynyl | —CONH— | 2-methylthioethyl | 0.33 | 245–250 |
| 7(4) | prop-2-ynyl | —CONH— | 3-hydroxypropyl | 0.5 | 229–230 |
| 8(5) | prop-2-ynyl | —CONH— | 4-hydroxybutyl | 0.8 | 203–205 |
| 9(5) | prop-2-ynyl | —CONH— | 6-hydroxyhexyl | 1.0 | 213–215 |

Notes
(1) During the work-up trifluoroacetic acid was added before the centrifugation step. The product obtained contained 1.2 equivalents of trifluoroacetic acid.
(2) During the work-up trifluoroacetic acid was added before the centrifugation step and the product so obtained was purified by chromatography on a reversed phase hplc column eluting with a 80:20:0.1 v/v mixture of water:acetonitrile:trifluoroacetic acid. The product obtained contained 2.2 equivalents of trifluoroacetic acid.
(3) The product was not centrifuged, but was filtered off after the trituration step and washed copiously with water.
(4) After evaporation of the solvent the product was purified by trituration with hot ethanol and isolated by filtration.
(5) After removal of the solvent the sample was recrystallized from isopropanol.

EXAMPLE 5

3-Chloropropylamine hydrochloride (85 mg) and triethylamine (250 μl) were added successively to a mixture of p-[N-(3,4-dihydro-2-methyl-4-oxoquinazolin-6-ylmethyl)-N-(prop-2-ynyl)amino]benzoyl azide (200 mg) and N,N-dimethylformamide (4 ml) and the mixture was stirred in the absence of light at laboratory temperature for 4 hours. The solvent was evaporated under reduced pressure and the residual solid was triturated with water (70 ml) and the mixture was centrifuged. The supernatant liquid was decanted, the remaining solid was recentrifuged with water (70 ml), and the supernatant solution was again decanted. The solid was transferred to a round-bottomed flask and was freeze-dried overnight and then dried in vacuo at 70° C. for 12 hours. There was thus obtained N-(3-chloropropyl)-p-[N-3,4-dihydro-2-methyl-4-oxoquinazoline-6-ylmethyl)-N-(prop-2-ynyl)amino]benzamide (0.175 g) m.p. 205°–215° C.

NMR Spectrum: (CD$_3$SOCD$_3$) 1.94 (quintet, 2H, CH$_2$, J=7 Hz), 2.33 (s,3H, 2—CH$_3$), 3.18 (t, 1H, C≡CH, J=2 Hz), 3.32 (q, 2H, CH$_2$NH, J=7 Hz), 3.65 (t, 2H, CH$_2$Cl, J=7Hz), 4.31 (d, 2H, CH$_2$C≡CH, J=2Hz), 4.74 (s, 2H, ArCH$_2$N), 6.82, (d, 2H, aromatic, J=8 Hz), 7.52 (d, 1H, 8H, J=8 Hz), of d s, 1H, 7H, J=8 and 2Hz), 7.68 (d, 2H, aromatic, J=8 Hz), 7.95 (d, 1H, J=2 Hz), 8.15 (t, 1H, CONH, J=7 Hz), 12.13 (broad s, 1H, NH (3-H)); Mass Spectrum: (positive ion FAB) m/e (P+1) 423 (base peak); Elemental Analysis: Found C, 64.8; H, 5.4; N, 13.8; C$_{23}$H$_{23}$N$_4$O$_2$Cl requires C, 65.3; H, 5.5; N, 13.3%.

EXAMPLE 6

The process described in Example 5 was repeated using the appropriate amine or amine hydrochloride in place of 3-chloropropylamine hydrochloride. There were thus obtained the compounds described in the following table, the structures of which were confirmed by proton magnetic resonance and mass spectroscopy and by element analysis.

oyl azide (150 mg) and N,N-dimethylformaide (1 ml) and the mixture was stirred in the absence of light at laboratory temperature for 3 hours. The solvent was evaporated under reduced pressure. The residue was dissolved in dimethylsulphoxide (2 ml), the mixture was acidified by the dropwise addition of trifluoroacetic acid and then diluted with water (2 ml). This mixture was chromatographed in two portions on a reversed-phase hplc column (Dynamax C-18 reversed-phase preparative column) eluting with a 80:20:0.1 v/v mixture of acetonitrile:water:trifluoroacetic acid. Fractions were monitored by analytical hplc and pure fractions were combined, evaporated and then freeze-dried to give an oil which crystallized upon trituration with acetonitrile. There was thus obtained p-N-3,4-dihydro-2-methyl-4-oxoquinazolin-6-dimethyl)-N-(prop-2-ynyl)amino]-N-(5-aminopentyl)benzamide (167 mg), m.p. 128°–130° C.

NMR Spectrum: (CD$_3$SOCD$_3$) 1.22 1.65 (m, 6H, —CH$_2$CH$_2$CH$_2$ ), 2.37 (s, 3H, 2—CH$_3$), 2.78 (m, 2H, CH$_2$NH$_2$), 3.18 (t, 1H, CaCH, J=2 Hz), 3.22 (q, 2H, CONHCH2, J=7 Hz), 3.9–4.6 (broad, 3H+H$_2$O peak, NH and NH$_2$), 4.31 (d, 2H, CH$_2$C≡CH, J=2 Hz), 4.77 (s, 2H, ArCH$_2$N), 6.82 (d, 2H, aromatic, J=8 Hz), 7.56 (d, 1H, 8-H, J=8 Hz), 7.69 (d, 2H, aromatic, J=8 Hz), 7.72 (d of d's, 1H, 7-H, J=8 and 2 Hz), 7.98 (d, 1H, 5-H, J=2 Hz), 8.07 (t, 1H, CONH, J=7 Hz); Mass Spectrum: (positive ion FAB) m/e (P+1) 432; Elemental Analysis: Found C, 48.5; H, 4.2; N, 9.0; C$_{25}$H$_{29}$N$_5$O$_2$ 0.3CF$_3$CO$_2$H requires C, 48.1; H, 4.2; N, 9.1%.

EXAMPLE 8

The process described in Example 7 was repeated

TABLE III

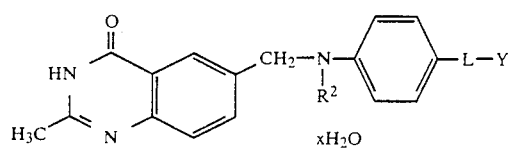

| Compd. No. (Note) | R$^2$ | L | Y | x | m.p. (°C.) |
|---|---|---|---|---|---|
| 1(1) | prop-2-ynyl | —CONH— | 2-(t-butylthio)-ethyl | 0.33 | 182–184 |
| 2(2) | prop-2-ynyl | —CONH— | 5-cyanopentyl | 0.5 | 206–210 |
| 3(3) | prop-2-ynyl | —CONH— | 2-mercaptoethyl | 0.2 | 205–212 (decomp.) |
| 4(4) | prop-2-ynyl | —CONH— | 2-hydroxyethyl | 1.0 | 235–245 |
| 5(4) | prop-2-ynyl | —CONH— | 2-aminoethyl | 1.5 | 140–144 |

(1) The product was obtained by filtration rather than by centrifugation.
(2) 1,8-Diazabicyclo[5.4.0]undec-7-ene was used as the base in place of triethylamine.
(3) Ethanethiol was added after removal of the solvent and before the addition of water for the centrifugation step to suppress the formation of disulphides.
(4) DMSO was used in place of N,N-diethylformamide as the reaction solvent.

EXAMPLE 7

1,5-Diaminopentane (165 mg,) and 1,8-diazabicyclo[5.4.0]-undec-7-ene (122 mg) were added successively to a mixture of p-[N-3,4-dihydro-2-methyl-4-oxoquinazolin-6-ylmethyl)-N-(prop-2-ynyl)amino]benzusing the appropriate amine in place of 1,5-diaminopentane. There were thus obtained the compounds described in the following table, the structures of which were confirmed by proton magnetic resonance and mass spectroscopy and by elemental analysis.

TABLE IV

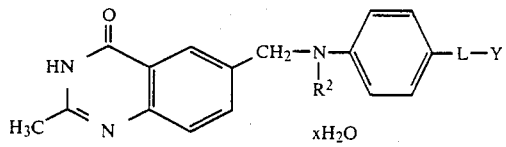

| Compd. No. (Note) | R² | L | Y | x | m.p. (°C.) |
|---|---|---|---|---|---|
| 1(1) | prop-2-ynyl | —CONH— | 3-aminopropyl | | 224–226 |
| 2(2) | prop-2-ynyl | —CONH— | 4-aminobutyl | 0.5 | 144–180 |
| 3(3) | prop-2-ynyl | —CONH— | 2-cyanoethyl | | 277.5–279 |
| 4(4) | prop-2-ynyl | —CONMe— | cyanomethyl | 0.33 | 214–215 |
| 5(5) | prop-2-ynyl | —CONMe— | 2-cyanoethyl | | Gum |
| 6(6) | prop-2-ynyl | —CONH— | 6-aminohexyl | | 150–177 |

Notes
(1) The product contained 1.5 equivalents of trifluoroacetic acid.
(2) The product was purified by medium-pressure column chromatography using a reversed-phase column and decreasingly polar mixtures of water and methanol (to 5:95 v/v) as eluent. The product contained 0.5 equivalents of methanol.
(3) The appropriate diamine was added as a hemifumarate salt. After the hplc purification step the product was further purified by medium-pressure column chromatography. The product contained 0.1 equivalents of trifluoroacetic acid.
(4) The appropriate amine was added as its hydrochloride salt. The product was purified by medium pressure chromatography using increasingly polar mixtures of methylene chloride and ethanol (from 97:3 to 85:15 v/v) as eluent.
(5) The product contained 1.5 equivalents of trifluoroacetic acid.
(6) The product contained 2 equivalents of trifluoroacetic acid.

EXAMPLE 9

Sodium hydroxide (1 ml of a 1.0M solution) was added to a mixture of p-[N-(3,4-dihydro-2-methyl-4-oxo-3-(pivaloyloxymethyl) quinazolin-6-dimethyl)-N-(prop-2-ynyl)amino]-N-(prop-2-ynyl)benzamide (120 mg) in ethanol (5 ml) and the mixture was stirred at laboratory temperature for 2 hours. Water (5 ml) was added and solvents were evaporated under reduced pressure. The residue was dried in vacuo and powdered. Water (50 ml) was added, and the resultant mixture was centrifuged. The supernatant liquid was discarded and the centrifugation process was repeated (three times) until the pH of the aqueous supernatant was neutral. The residue was then freeze-dried. There was thus obtained p-[N-(3,4-dihydro-2-methyl-4-oxoquinazolin-6-ylmethyl)-N-(prop-2-ynyl)amino-N-(prop-2-ynyl)benzamide (50 mg), m.p. 250°–260° C.

NMR Spectrum: (CD₃SOCD₃) 2.32 (s, 3H, CH₃), 3.00 (t, 1H, C≡CH, J=2 Hz), 3.16 (t, 1H, C≡CH, J=2 Hz), 3.99 (d of d's, 2H, NHCH₂C≡CH, J=5 and 2 Hz), 4.30 (d, 2H, NCH₂C≡CH, J=2 Hz), 4.75 (s, 2H, ArCH₂N), 6.82 (d, 2H, aromatic, J=8 Hz), 7.52 (d, 1H, 8H, J=8 Hz), 7.68 (d of d's, 1H, 7H, J=8 and 2 Hz), 7.71 (d, 2H, aromatic, J=8 Hz), 7.95 (d, 1H, 5H, J=2 Hz), 8.52 (t, 1H, CONH, J=5 Hz); Mass Spectrum: (positive ion FAB) m/e (P+1) 385; Elemental Analysis: Found C, 68.9, H, 5.4, N, 13.5, C₂₃H₂₀N₄O₂. H₂O requires C, 68.6; H, 5.5; N, 13.9%. The required benzamide starting material was obtained as follows: Oxalyl chloride (127 mg) was added dropwise to a stirred mixture of p-[N-(3,4-dihydro-2-methyl-4-oxo-3-(pivaloyloxymethyl)quinazoline-6-ylmethyl)-N-(prop-2-ynyl)amino]benzoic acid (300 mg), dichloromethane (7 ml) and N,N-dimethylformamide (3 drops). The reaction was stirred under an atmosphere of argon for 2 hours at laboratory temperature. Solvents were evaporated under reduced pressure and a mixture of triethylamine (203 mg), 2-propynylamine (73.8 mg) and dichloromethane (8 ml) was added. The mixture was stirred at laboratory temperature for 12 hours. The mixture was washed with water (3×7 ml), saturated aqueous sodium hydrogen carbonate solution (7 ml) and a saturated aqueous sodium chloride solution (7 ml), dried (MgSO₄) and evaporated under reduced pressure to give a foam (283 mg) which was purified by chromatography on silica gel eluting initially with ethyl acetate:hexane (1:1; 100 ml), then with ethyl acetate:hexane (3:1; 100 ml) and finally with ethyl acetate. There was thus obtained p-[N-3,4-dihydro-2-methyl-4-oxo-3-(pivaloyloxymethyl)quinazoline-6-ylmethyl)-N-(prop-2-ynyl)amino](-prop-2-ynyl)benzamide (126 mg) as a gum.

NMR Spectrum: (CDCl₃) 1.22 (s, 9H, t-Bu), 2.26 (t, 1H, C≡CH, J=2 Hz), 2.66 (s, 3H, 2—CH₃), 4.14 (d, 2H, CH₂C≡CH, J=2 Hz), 2.28 (t, 1H, C≡CH, J=2 Hz) CH₂C≡CH, J=2 Hz), 4.23 (d of d's, 2H, NHCH₂C≡CH, J=5 Hz and 2 Hz), 4.74 (s, 2H, ArCH₂N), 6.10 (s, 2H, OCH₂N), 6.11 (t, 1H, CONH, J=5 Hz), 6.84 (d, 2H, aromatic, J=8 Hz), 7.64 (d, 1H, 8H, J=8 Hz), 7.68 (d, 2H, aromatic, J=8 Hz), 7.69 (d of d's, 1H, 7H, J=8 and 2 Hz), 8.18 (d, 1H, 5H, J=2 Hz); Mass Spectrum: (positive ion FAB) m/e (P+1) 499.

EXAMPLE 10

The process described in Example 9 was repeated using the appropriate amine in place of 2-propynylamine in the preparation of starting materials. There were thus obtained the compounds described in the following table, the structures of which were confirmed by proton magnetic resonance and mass spectroscopy and by elemental analysis.

TABLE V

[Structure: quinazoline with HN-C(=O), H3C-C=N, CH2-N(R2)-phenyl-L-Y, xH2O]

| Compd. No. (Note) | R² | L | Y | x | m.p. (°C.) |
|---|---|---|---|---|---|
| 1 | prop-2-ynyl | —CONH— | allyl | 0.5 | 252-254 |
| 2 | prop-2-ynyl | —CONH— | (cyclohexyl)-methyl | 0.7 | 251-252 |
| 3(1) | prop-2-ynyl | —CONH— | t-butyl | 0.5 | 242-250 |
| 4 | prop-2-ynyl | —CONH— | 2,2,2-trifluoro-ethyl | 1.75 | 302-306 |

Notes
(1) This product was not isolated by centrifugation from aqueous solution but was purified by column chromatography on silica gel eluting with ethyl acetate.

EXAMPLE 11

3-Chloroperbenzoic acid (34.5 mg) was added dropwise, as a solution in N,N-dimethylformamide (1 ml), to a solution of p-[N-(3,4-dihydro-2-methyl-4-oxoquinazolin-6-ylmethyl)-N-(prop-2-ynyl)amino]-N-( 2-tert-butyl-thioethyl)benzamide (95 mg) in N,N-dimethylformamide (2 ml) and the mixture was stirred at 5° C. for 2 hours. The mixture was evaporated and the residue was chromatographed on silica eluting with dichloromethane:methanol (90:10 v/v). The product so obtained was triturated with diethyl ether and dried. There was thus obtained p-[N-(3,4-dihydro-2-methyl-4-oxoquinazolin-6-ylmethyl)-N-(prop-2-ynyl)amino-N-(2-tert-butylsulphinylethyl)benzamide (73 mg), m.p. 144°-155° C. (decomp.).

NMR Spectrum, (CD$_3$SOCD$_3$) 1.14 (s, 9H, 3×CH$_3$), 2.33 (s, 3H, 2-CH$_3$), 2.52 (d of t's, 1H, HCSO, J=9 and 7 Hz), 2.91 (d of t's, 1H, HCSO, J=9 and 7 Hz), 3.17 (t, 1H, C≡CH, J=2 Hz), 3.62 (m, 2H, CONHCH$_2$), 4.30 (d, 2H, CH$_2$C≡C, J=2 Hz), 4.76 (s, 2H, CH$_2$N), 6.83 (d, 2H, aromatic, J=9 Hz), 7.52 (d, 1H, 8H, J=8 Hz), 7.70 (d of d's, 1H, 7-H, J=8 Hz and 2 Hz), 7.72 (d, 2H, aromatic, J=9 Hz), 7.95 (d, 1H, 5-H, J=2 Hz), 8.38 (t, 1H, CONH, J=6 Hz), 12.0 (broad s, 1H, 3-H, (NH)); Mass Spectrum: (positive ion FAB) m/e (P+1) 479; Elemental Analysis: Found C, 63.0; H, 6.4; N, 10.9; C$_{26}$H$_{30}$N$_4$O$_3$S. H$_2$O requires C, 62.9; H, 6.5; N, 11.3%.

The procedure described immediately above was repeated except that p-[N-(3,4-dihydro-2-methyl-4-oxoquinazolin-6-ylmethyl) N-prop-2-ynyl)amino]-N-(2-methylthioethyl)benzamide (81 mg) was used as the benzamide starting material. There was thus obtained p-[N-(3,4-dihydro-2-methyl-4-oxoquinazolin-6-ylmethyl)-N-(prop-2-ynyl)amino]-N-(2-methylsulphinylethyl)benzamide (49 mg), m.p. 210°-214° C. (decomp.).

EXAMPLE 12

3-Chloroperbenzoic acid (69 mg) was added dropwise, as a solution in N,N-dimethylformamide (2 ml) to a solution of p-[N-(3,4-dihydro-2-methyl-4-oxoquinazolin-6-ylmethyl) N-(prop-2-ynyl)amino-N-(2-methylthioethyl)benzamide (81 mg) in N,N-dimethylformamide (2 ml) and the mixture was stirred at 5° C. for 3 hours. The mixture was evaporated and the residue was triturated with diethyl ether (2×8 ml). The resulting solid was dissolved in dimethylsuphoxide (1 ml), trifluoroacetic acid was added until the solution was acidified to pH 1. Methanol (1.5 ml) and water (17 ml) were added and the mixture was stirred for 10 minutes. The precipitate was isolated by centrifugation, washed with water (3×10 ml) and freeze-dried. There was thus obtained p-[N-(3,4-dihydro-2-methyl-4-oxoquinazolin-6-ymethyl)-N-(prop-2-ynyl)amino]-N-(2-methylsulphonylethyl)benzamide, containing 1.05 equivalents of trifluoroacetic acid (67 mg), m.p. 198°-202° C. (decomposes).

NMR Spectrum: (CD$_3$SOCD$_3$) 2.37 (s, 3H, 2-CH$_3$), 2.99 (s, 3H, SO$_2$CH$_3$), 3.17 (t, 1H, C≡CH, J=2 Hz), 3.32 (t, 2H, CH$_2$SO$_2$, J=7 Hz), 3.63 (q, 2H, NHCH$_2$, J=7 Hz), 4.31 (d, 2H, NCH$_2$C≡CH, J=2 Hz), 4.78 (s, 2H, ArCH$_2$N), 6.83 (d, 2H, aromatic, J=8 Hz), 7.55 (d, 1H, 8-H, J=8 Hz), 7.68 (d, 2H, aromatic, J=8 Hz), 7.71 (d of d's, 1H, 7-H, J=8 and 2 Hz), 7.98 (d, 1H, 5-H, J=2 Hz), 8.33 (t, 1H, NHCH$_2$, J=7 Hz), 12.0 (broad s, 1H, NH (3—H)); Mass Spectrum: (positive ion FAB) m/e (P+1) 453; Elemental Analysis: Found C, 53.0; H, 4.6; N, 9.7; C$_{23}$H$_{24}$N$_4$SO$_4$. 1.05CF$_3$CO$_2$H requires C, 52.7; H, 4.4; N, 9.8%.

Note: The p-[N(3,4-dihydro-2-methyl-4-oxo-3-(pivaloyloxymethyl)quinazol)-6-ylmethyl)-N-(prop-2-ynyl)amino]benzoic acid used as a starting material in Example 9 above was obtained as follows:

A mixture of tert-butyl 4-(prop-2-ynyl)aminobenzoate (16 g; European Patent Application No. 239362), 6-bromomethyl-3,4-dihydro-2-methyl-4-oxo-3-(pivaloyloxymethyl)quinazoline (80 g; European Patent Application No. 239362), 2,6 lutidine (10 ml) and N,N-dimethylacetamide (450 ml) was heated overnight to 55° C. under an atmosphere of argon. The mixture was poured into water (400 ml) and extracted with methylene chloride (2×300 ml). The organic extracts were combined, washed with water, dried (MgSO$_4$) and evaporated. The residue was purified by column chromatography on silica using initially a 7:3 v/v mixture of hexane and ethyl acetate and then a 1:1 v/v mixture of hexane and ethyl acetate as eluent.

A mixture of the product so obtained and trifluoroacetic acid (400 ml) was stirred at laboratory temperature for 40 minutes. The solvent was evaporated and the residue was purified by column chromatography on silica using initially a 9:1 v/v mixture of hexane acetone, then a 4:1 v/v mixture of hexane and acetone and finally methylene chloride as eluent. There was thus obtained p-[N-(3,4-dihydro-2-oxo-3-(pivaloyloxymethyl)-quinazolin-6-ylmethyl)-N-(prop-2-ynyl)amino]benzoic acid (26.3 g).

CHEMICAL FORMULAE

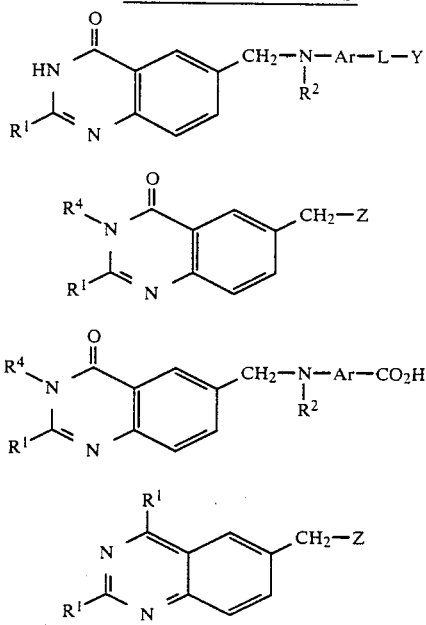

What we claim is:
1. A quinazoline of the formula I

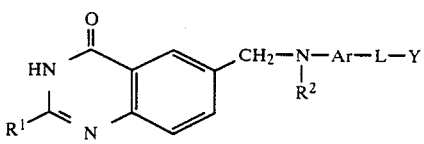

wherein $R^1$ is hydrogen or amino, or alkyl or alkoxy each of up to 6 carbon atoms;
or $R^1$ is alkyl of up to 3 carbon atoms which bears a hydroxy substituent, or which bears one, two or three fluoro substituents;
or $R^1$ is hydroxyalkoxy of up to 3 carbon atoms or alkoxyalkoxy of up to 6 carbon atoms;
wherein $R^2$ is hydrogen, alkyl, alkenyl, alkynyl, hydroxyalkyl or halogenoalkyl each of up to 6 carbon atoms:
wherein Ar is phenylene or heterocyclene which may be unsubstituted or may bear one or two substituents selected from halogeno, hydroxy and amino;
wherein L is a group of the formula —CO.NH— or —CO.NR$_3$—,
wherein $R^3$ Is alkyl of up to 6 carbon atoms; and
wherein Y is hydrogen or alkyl, cycloalkyl, alkenyl or alkynyl each of up to 6 carbon atoms; or
Y is a group of the formula —A—Y$^1$ in which A is alkylene of up to 6 carbon atoms, and Y$^1$ is hydroxy, amino, nitro, cyano, mercapto or halogeno, or alkoxy, alkylamino, dialkylamino, halogenoalkyl, alkylthio, alkylsulphinyl, alkylsulphonyl or cycloalkyl each of up to 6 carbon atoms;
and provided that, in the group of the formula —L—Y, no constituent methylene or methine group is attached to more than one heteroatom; or a pharmaceutically-acceptable salt thereof.
2. A quinazoline of the formula I as claimed in claim 1 wherein $R^1$ is alkyl or alkoxy each of up to 6 carbon atoms;
or $R^1$ is alkyl of up to 3 carbon atoms which bears a hydroxy substituent, or which bears one, two or three fluoro substituents;
or $R^1$ is hydroxyalkoxy of up to 3 carbon atoms or alkoxyalkoxy of up to 6 carbon atoms;
wherein $R^2$ is hydrogen, alkyl, alkenyl, alkynyl, hydroxyalkyl or halogenoalkyl each of up to 6 carbon atoms;
wherein Ar is phenylene or heterocyclene which may be unsubstituted or may bear one or two substituents selected from halogeno, hydroxy and amino;
wherein L is a group of the formula —CO.NH— or —CO.NR$_3$—,
wherein $R^3$ is alkyl of up to 6 carbon atoms; and
wherein Y is hydrogen or alkyl, cycloalkyl, alkenyl or alkynyl each of up to 6 cazbon atoms; or
Y is a group of the formula A—Y$^1$ in which A is alkylene of up to 6 carbon atoms, and Y$^1$ is hydroxy, amino, nitro or cyano, or alkoxy, alkylamino, dialkylamino, halogenoalkyl, alkylthio, alkylsulphinyl or alkylsulphonyl each of up to 6 carbon atoms; and provided that, in the group of the formula —L—Y, no constituent methylene or methine group is attached to more than one heteroatom and no constituent methylidene or methylidyne group is attached to a heteroatom;
or a pharmaceutically-acceptable salt thereof.
3. A quinazoline of the formula I as claimed in claim 1 wherein $R^1$ is hydrogen, amino, methyl, ethyl, methoxy or fluoromethyl;
wherein $R^2$ is hydrogen, methyl, ethyl, propyl, prop-2-enyl, prop-2-ynyl, 2-hydroxyethyl, 3-hydroxypropyl, 2-fluoroethyl or 2-bromoethyl;
wherein Ar is 1,4-phenylene, thien-2,5-diyl, pyrid-2,5-diyl or thiazol-2,5-diyl which is unsubstituted or which bears one or two substituents selected from fluoro, chloro, hydroxy and amino;
wherein L is a group of the formula —CO.NH— or —CO.NR$_3$—, wherein $R^3$ is methyl or ethyl; and
wherein Y is hydrogen, methyl, ethyl, propyl, isopropyl, isobutyl or tert-butyl; or Y is a group of the formula —A—Y$^1$ in which A is methylene, ethylene, ethylidene, trimethylene, propylene, 2-trifluoromethylethylene, 1-isopropylethylene, tetramethylene, pentamethylene or hexamethylene and Y$^1$ is hydroxy, amino, nitro, cyano, mercapto, chloro, methoxy, methylamino, ethylamino, butylamino, dimethylamino, diethylamino, methylthio, ethylthio, propylthio, isopropylthio, tert-butylthio, methylsulphinyl, ethylsulphinyl, isopropylsulphinyl, tert-butylsulphinyl or methylsulphonyl;
or a pharmaceutically-acceptable salt thereof.
4. A quinazoline of the formula I as claimed in claim 1 wherein
$R^1$ is methyl;
$R^2$ is methyl, ethyl or prop-2-ynyl;
Ar is 1,4-phenylene;
L is a group of the formula —CO.NH—; and
Y is propyl, isopropyl or isobutyl; or Y is a group of the formula —A—Y$^1$ in which A is methylene, ethylene, trimethylene, 2-methylethylene, 2-trifluoromethylethylene, 1-isopropylethylene, tetramethylene or pentamethylene and Y$^1$ is hydroxy, amino, cyano, chloro, methoxy, butylamino, dimethylamino, diethylamino, methylthio, ethylthio, methylsulphinyl or methylsulphonyl; or a pharmaceutically-acceptable salt thereof.

5. A quinazoline of the formula I as claimed in claim 1 wherein R¹ is methyl;
wherein R² is hydrogen, methyl, ethyl, prop-2-ynyl or 2-fluoroethyl;
wherein Ar is 1,4-phenylene or thien-2,5-diyl, or is pyrid-2,5-diyl or thiazol-2,5-diyl each with the group —L—Y In the 2-position, or is 2-fluoro-1,4-phenylene with the group —L—Y in the 1-position;
wherein L is a group of the formula —CO.NH—; and
wherein Y is hydrogen, methyl, ethyl, propyl, isopropyl or isobutyl;
or a pharmaceutically-acceptable salt thereof.

6. A quinazoline of the formula I as claimed in claim 1 wherein R¹ is methyl; R² is ethyl or prop-2-ynyl; Ar is 1,4-phenylene;
L is a group of the formula —CO.NH—;
and Y is propyl, isobutyl, 2-hydroxy-2-trifluoromethylethyl, 2-hydroxy-1-isopropylethyl, 2-hydroxyethyl, 3-hydroxypropyl, 4-hydroxybutyl, 6-hydroxyhexyl, 2-aminoethyl, cyanomethyl, 2-cyanoethyl, 5-cyanopentyl, 3-chloropropyl, 2-methoxyethyl, 2-butylaminoethyl, 2-dimethylaminoethyl, 3-dimethylaminopropyl, 3-diethylaminopropyl, 2-methylthioethyl, 2-ethylthioethyl, 2-methylsulphinylethyl or 2-methylsulphonylethyl;
or a pharmaceutically-acceptable salt thereof.

7. A quinazoline selected from the group of compounds:
p-N[-(3,4-dihydro-2-methyl-4-oxoquinazoline-6-ylmethyl)-N-(prop-2-ynyl)amino]-N-propylbenzamide,
N-cyanomethyl-p-[N-(3,4-dihydro-2-methyl-4-oxoquinazolin-6-ylmethyl)-N-(prop-2-ynyl)amino]-benzamide,
p-[N-(3,4-dihydro-2-methyl-4-oxoquinazolin-6-dimethyl)-N-(prop-2-ynylamino]-N-(2-hydroxy-2-trifluoromethylethyl)benzamide,
p-[N-(3,4-dihydro-2-methyl-4-oxoquinazolin-6-ylmethyl)-N-(prop-2-ynyl)amino]-N-(2-ethylthioethyl)benzamide,
p-[N-(3,4-dihydro-2-methyl-4-oxoquinazoline-6-ylmethyl)-N-(prop-2-ynyl)amino-N-(2-methoxyethyl)benzamide,
N-(2-N-butylaminoethyl)-p-[N-(3,4-dihydro-2-methyl-4-oxoquinazolin-6-ylmethyl)-N-(prop-2-ynyl)amino]-benzamide,
p-[N-(3,4-dihydro-2-methyl-4-oxoquinazolin-6-dimethyl)-N-(prop-2-ynyl)amino]-N-(2-N,N-dimethylaminoethyl)benzamide,
p-[N-(3,4-dihydro-2-methyl-4-oxoquinazolin-6-ylmethyl)-N-(prop-2-ynyl)amino]-N-(3-N,N-dimethylaminopropyl)benzamide,
N-(3-N,N-diethylaminopropyl)-p-[N-(3,4-dihydro-2-methyl-4-oxoquinazolin-6-ylmethyl)-N-(prop-2-ynyl)amino]benzamide,
p-[N-(3,4-dihydro-2-methyl-4-oxoquinazoline-6-ylmethyl)-N-(prop-2-ynyl)amino]-N-(2-methylthioethyl)-benzamide,
p-[N-(3,4-dihydro-2-methyl-4-oxoquinazolin-6-ylmethyl) N-(prop-2-ynyl)amino]-N-( 2-hydroxyethyl)benzamide,
p-[N-(3,4-dihydro-2-methyl-4-oxoquinazolin-6-ylmethy-N-(prop-2-ynyl)amino]-N-(3-hydroxypropyl)benzamide,
p-[N-(3,4-dihydro-2-methyl-4-oxoquinazolin-6-ylmethyl)-N-(prop-2-ynyl)amino]-N-(4-hydroxybutyl)-benzamide,
p-[N-(3,4-dihydro-2-methyl-4-oxoquinazolin-6-ylmethyl-N-(prop-2-ynyl)amino]-N-(6-hydroxyhexyl)benzamide,
N-(3-chloropropyl)-p-[N-(3,4-dihydro-2-methyl-4-oxoquinazolin-6-ylmethyl)-N-(prop-2-ynyl)amino]-benzamide,
N-(2-aminoethyl)-p-[N-(3,4-dihydro-2-methyl-4-oxoquinazolin-6-ylmethyl)-N-(prop-2-ynyl)amino]-benzamide,
N-(5-cyanopentyl)-p-[N-(3,4-dihydro-2-methyl-4-oxoquinazolin-6-ylmethyl)-N-(prop-2-ynyl)amino]-benzamide and
N-(2-cyanoethyl)-p-[N-(3,4-dihydro-2-methyl-4-oxoquinazolin-6-ylmethyl)-N-(prop-2-ynyl)amino]-benzamide.

8. A pharmaceutical composition which comprises a quinazoline as claimed in claim 1, or a pharmaceutically-acceptable salt thereof, in association with a pharmaceutically-acceptable diluent or carrier.

9. A method for producing an anti-tumour effect in a warm-blooded animal in need of such treatment which comprises administering to said animal an effective amount of a quinazoline of the formula I as claimed in any one of claims 1 to 7, or a pharmaceutically-acceptable salt thereof.

* * * * *